United States Patent
Aranyi

(10) Patent No.: US 11,272,932 B2
(45) Date of Patent: *Mar. 15, 2022

(54) STRUCTURE FOR ATTACHING BUTTRESS MATERIAL TO ANVIL AND CARTRIDGE OF SURGICAL STAPLING INSTRUMENT

(71) Applicant: Covidien LP, Mansfield, MA (US)

(72) Inventor: Ernie Aranyi, Easton, CT (US)

(73) Assignee: Covidien LP, Mansfield, MA (US)

( * ) Notice: Subject to any disclaimer, the term of this patent is extended or adjusted under 35 U.S.C. 154(b) by 297 days.

This patent is subject to a terminal disclaimer.

(21) Appl. No.: 16/530,210

(22) Filed: Aug. 2, 2019

(65) Prior Publication Data

US 2019/0350585 A1 Nov. 21, 2019

Related U.S. Application Data

(63) Continuation of application No. 15/454,043, filed on Mar. 9, 2017, now Pat. No. 10,368,868.

(51) Int. Cl.
*A61B 17/072* (2006.01)
*A61B 17/068* (2006.01)
(Continued)

(52) U.S. Cl.
CPC ...... *A61B 17/07207* (2013.01); *A61B 5/6858* (2013.01); *A61B 17/068* (2013.01);
(Continued)

(58) Field of Classification Search
CPC ............... A61B 17/068; A61B 17/072; A61B 17/07207; A61B 17/07292; A61B 17/115;
(Continued)

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2282761 A1 9/1998
DE 19924311 A1 11/2000
(Continued)

OTHER PUBLICATIONS

European Office Action corresponding to counterpart Int'l Appln. No. EP 14 17 2681.0 dated May 13, 2016.
(Continued)

*Primary Examiner* — Scott A Smith
(74) *Attorney, Agent, or Firm* — Carter, DeLuca & Farrell LLP

(57) ABSTRACT

An end effector of a surgical stapler includes first and second jaw members and a buttress material. The first jaw member is moveable relative to the second jaw member. The first jaw member includes a contact surface, a first projection, and a catch. The catch includes first and second fingers distal of the first projection. The second finger is biased toward the contact surface. The buttress material defines a longitudinal axis. The buttress material is releasably secured to the first jaw member. The buttress material defines first, second, and third slots formed therein. The first projection of the first jaw member is received in the first slot of the buttress material. The first finger of the catch is received in the second slot of the buttress material.

19 Claims, 10 Drawing Sheets

(51) Int. Cl.
*A61B 5/00* (2006.01)
*A61B 17/00* (2006.01)

(52) U.S. Cl.
CPC ...... *A61B 17/072* (2013.01); *A61B 17/07292* (2013.01); *A61B 5/6859* (2013.01); *A61B 2017/00893* (2013.01); *A61B 2017/07214* (2013.01); *A61B 2017/07271* (2013.01)

(58) Field of Classification Search
CPC A61B 2017/07214; A61B 2017/07271; A61B 2017/07285
USPC .............. 227/19, 175.1, 175.2, 176.1, 180.1; 606/1, 139, 29, 153, 219
See application file for complete search history.

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |

(56) References Cited

U.S. PATENT DOCUMENTS

| | | |
|---|---|---|
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,052,699 B1 | 11/2011 | Sherwinter |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,236,015 B2 | 8/2012 | Bettuchi et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,292,154 B2 | 10/2012 | Marczyk |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,071 B1 | 11/2012 | Knodel |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,395,514 B2 | 3/2013 | Linsenmaier et al. |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,691 B2 | 10/2013 | Leen et al. |
| 8,556,918 B2 | 10/2013 | Bauman et al. |
| 8,561,873 B2 | 10/2013 | Ingmanson et al. |
| 8,584,492 B2 | 11/2013 | Seo et al. |
| 8,584,920 B2 | 11/2013 | Hodgkinson |

(56) References Cited

U.S. PATENT DOCUMENTS

| | | |
|---|---|---|
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,657,176 B2 | 2/2014 | Shelton, IV et al. |
| 8,663,258 B2 | 3/2014 | Bettuchi et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,721,703 B2 | 5/2014 | Fowler |
| 8,740,037 B2 | 6/2014 | Shelton, IV et al. |
| 8,740,038 B2 | 6/2014 | Shelton, IV et al. |
| 8,746,535 B2 | 6/2014 | Shelton, IV et al. |
| 8,752,699 B2 | 6/2014 | Morgan et al. |
| 8,757,466 B2 | 6/2014 | Olson et al. |
| 8,777,004 B2 | 7/2014 | Shelton, IV et al. |
| 8,789,737 B2 | 7/2014 | Hodgkinson et al. |
| 8,820,606 B2 | 9/2014 | Hodgkinson |
| 8,821,523 B2 | 9/2014 | Heinrich et al. |
| 8,857,694 B2 | 10/2014 | Shelton, IV et al. |
| 8,870,050 B2 | 10/2014 | Hodgkinson |
| 8,899,462 B2 | 12/2014 | Kostrzewski et al. |
| 8,920,443 B2 | 12/2014 | Hiles et al. |
| 8,920,444 B2 | 12/2014 | Hiles et al. |
| 8,925,782 B2 | 1/2015 | Shelton, IV |
| 8,926,658 B1 | 1/2015 | Knodel |
| 8,939,344 B2 | 1/2015 | Olson et al. |
| 8,956,390 B2 | 2/2015 | Shah et al. |
| 8,967,448 B2 | 3/2015 | Carter et al. |
| 8,978,954 B2 | 3/2015 | Shelton, IV et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,542 B2 | 4/2015 | Shelton, IV et al. |
| 9,016,543 B2 | 4/2015 | (Prommersberger) Stopek et al. |
| 9,016,544 B2 | 4/2015 | Hodgkinson et al. |
| 9,016,545 B2 | 4/2015 | Aranyi et al. |
| 9,027,817 B2 | 5/2015 | Milliman et al. |
| 9,033,203 B2 | 5/2015 | Woodard, Jr. et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 9,433,412 B2 | 9/2016 | Bettuchi et al. |
| 9,433,413 B2 | 9/2016 | Stopek |
| 10,368,868 B2 | 8/2019 | Aranyi |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0093029 A1 | 5/2004 | Zubik et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0143756 A1 | 6/2005 | Jankowski |
| 2005/0149073 A1 | 7/2005 | Arani et al. |
| 2005/0154093 A1 | 7/2005 | Kwon et al. |
| 2005/0228446 A1 | 10/2005 | Mooradian et al. |
| 2005/0245965 A1 | 11/2005 | Orban, III et al. |
| 2006/0004407 A1 | 1/2006 | Hiles et al. |
| 2006/0008505 A1 | 1/2006 | Brandon |
| 2006/0085030 A1 | 4/2006 | Bettuchi et al. |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0114262 A1 | 5/2007 | Mastri et al. |
| 2007/0123839 A1 | 5/2007 | Rousseau et al. |
| 2007/0175961 A1 | 8/2007 | Shelton et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |

(56) References Cited

U.S. PATENT DOCUMENTS

| | | |
|---|---|---|
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016888 A1 | 1/2010 | Calabrese et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0036895 A1 | 2/2011 | Marczyk et al. |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0089220 A1 | 4/2011 | Ingmanson et al. |
| 2011/0089375 A1 | 4/2011 | Chan et al. |
| 2011/0101070 A1 | 5/2011 | Bettuchi et al. |
| 2011/0139853 A1 | 6/2011 | Viola |
| 2011/0168759 A1 | 7/2011 | Prommersberger |
| 2011/0184444 A1 | 7/2011 | D'Agostino et al. |
| 2011/0215132 A1 | 9/2011 | Aranyi et al. |
| 2011/0215133 A1 | 9/2011 | Aranyi |
| 2011/0230901 A1 | 9/2011 | Bettuchi |
| 2011/0233259 A1 | 9/2011 | Olson |
| 2011/0278347 A1 | 11/2011 | Olson et al. |
| 2011/0282446 A1 | 11/2011 | Schulte et al. |
| 2011/0284615 A1 | 11/2011 | Tarinelli et al. |
| 2011/0290852 A1 | 12/2011 | Bettuchi et al. |
| 2011/0293690 A1 | 12/2011 | Griffin et al. |
| 2011/0297731 A1 | 12/2011 | Aranyi et al. |
| 2011/0315740 A1 | 12/2011 | Stopek |
| 2011/0315742 A1 | 12/2011 | Olson et al. |
| 2012/0035629 A1 | 2/2012 | Sherwinter |
| 2012/0067936 A1 | 3/2012 | Prommersberger |
| 2012/0074199 A1 | 3/2012 | Olson et al. |
| 2012/0080336 A1 | 4/2012 | Shelton, IV et al. |
| 2012/0080340 A1 | 4/2012 | Shelton, IV et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0083723 A1 | 4/2012 | Vitaris et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0145767 A1 | 6/2012 | Shah et al. |
| 2012/0168486 A1 | 7/2012 | Ingmanson et al. |
| 2012/0187179 A1 | 7/2012 | Gleiman |
| 2012/0197272 A1 | 8/2012 | Oray et al. |
| 2012/0228360 A1 | 9/2012 | Hodgkinson et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241505 A1 | 9/2012 | Alexander, III et al. |
| 2012/0273547 A1 | 11/2012 | Hodgkinson et al. |
| 2012/0273548 A1 | 11/2012 | Ma et al. |
| 2012/0273552 A1 | 11/2012 | Olson et al. |
| 2012/0298721 A1 | 11/2012 | Bettuchi et al. |
| 2012/0305626 A1 | 12/2012 | Stopek |
| 2012/0305629 A1 | 12/2012 | Orban, III et al. |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0037596 A1 | 2/2013 | Bear et al. |
| 2013/0037598 A1 | 2/2013 | Marczyk |
| 2013/0037600 A1 | 2/2013 | (Prommersberger) Stopek et al. |
| 2013/0075448 A1 | 3/2013 | Schmid et al. |
| 2013/0075450 A1 | 3/2013 | Schmid et al. |
| 2013/0105548 A1 | 5/2013 | Hodgkinson et al. |
| 2013/0105553 A1 | 5/2013 | (Tarinelli) Racenet et al. |
| 2013/0112731 A1 | 5/2013 | Hodgkinson |
| 2013/0112732 A1 | 5/2013 | Aranyi et al. |
| 2013/0112733 A1 | 5/2013 | Aranyi et al. |
| 2013/0112734 A1 | 5/2013 | Aranyi et al. |
| 2013/0126587 A1 | 5/2013 | Bettuchi et al. |
| 2013/0146641 A1 | 6/2013 | Shelton, IV et al. |
| 2013/0146643 A1 | 6/2013 | Schmid et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0214030 A1 | 8/2013 | Aronhalt et al. |
| 2013/0221062 A1 | 8/2013 | Hodgkinson |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0240600 A1 | 9/2013 | Bettuchi |

(56) References Cited

U.S. PATENT DOCUMENTS

| | | |
|---|---|---|
| 2013/0240601 A1 | 9/2013 | Bettuchi et al. |
| 2013/0240602 A1 | 9/2013 | Stopek |
| 2013/0256365 A1 | 10/2013 | Shelton, IV et al. |
| 2013/0256372 A1 | 10/2013 | Baxter, III et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256380 A1 | 10/2013 | Schmid et al. |
| 2013/0256382 A1 | 10/2013 | Swayze et al. |
| 2013/0277411 A1 | 10/2013 | Hodgkinson et al. |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0117066 A1 | 5/2014 | Aranyi et al. |
| 2014/0121686 A1 | 5/2014 | Viola |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek et al. |
| 2014/0166719 A1 | 6/2014 | Bettuchi et al. |
| 2014/0166721 A1 | 6/2014 | Stevenson et al. |
| 2014/0175156 A1 | 6/2014 | Hess et al. |
| 2014/0197223 A1 | 7/2014 | Hess et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0224857 A1 | 8/2014 | Schmid |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2014/0252066 A1 | 9/2014 | Shelton, IV et al. |
| 2014/0252068 A1 | 9/2014 | Shelton, IV et al. |
| 2014/0291380 A1 | 10/2014 | Weaner et al. |
| 2014/0361067 A1 | 12/2014 | Hodgkinson |
| 2015/0001276 A1 | 1/2015 | Hodgkinson et al. |
| 2015/0041347 A1 | 2/2015 | Hodgkinson |
| 2015/0076208 A1 | 3/2015 | Shelton, IV |
| 2015/0076212 A1 | 3/2015 | Shelton, IV |
| 2015/0090765 A1 | 4/2015 | Hess et al. |
| 2015/0097018 A1 | 4/2015 | Hodgkinson |
| 2015/0115015 A1 | 4/2015 | Prescott et al. |
| 2015/0119932 A1 | 4/2015 | Knodel |
| 2015/0122872 A1 | 5/2015 | Olson et al. |
| 2015/0129634 A1 | 5/2015 | Shelton, IV et al. |
| 2015/0133995 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196296 A1 | 7/2015 | Swayze et al. |
| 2015/0196297 A1 | 7/2015 | Stopek et al. |
| 2015/0196299 A1 | 7/2015 | Swayze et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |
| 2015/0238186 A1 | 8/2015 | Aronhalt et al. |
| 2015/0238187 A1 | 8/2015 | Schellin et al. |
| 2015/0238192 A1 | 8/2015 | Bettuchi et al. |
| 2015/0245835 A1 | 9/2015 | Racenet et al. |
| 2015/0282809 A1 | 10/2015 | Shelton, IV et al. |
| 2015/0297236 A1 | 10/2015 | Harris et al. |
| 2015/0305743 A1 | 10/2015 | Casasanta et al. |
| 2015/0327864 A1 | 11/2015 | Hodgkinson et al. |
| 2015/0327865 A1 | 11/2015 | Marczyk et al. |
| 2015/0335328 A1 | 11/2015 | Shelton, IV et al. |
| 2015/0342606 A1 | 12/2015 | Schmid et al. |
| 2015/0351753 A1 | 12/2015 | Shelton, IV et al. |
| 2015/0351754 A1 | 12/2015 | Harris et al. |
| 2015/0351757 A1 | 12/2015 | Harris et al. |
| 2015/0351758 A1 | 12/2015 | Shelton, IV et al. |
| 2015/0351761 A1 | 12/2015 | Shelton, IV et al. |
| 2015/0351764 A1 | 12/2015 | Shelton, IV |
| 2016/0000430 A1 | 1/2016 | Ming et al. |
| 2016/0000442 A1 | 1/2016 | Shelton, IV |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0066909 A1 | 3/2016 | Baber et al. |
| 2016/0066913 A1 | 3/2016 | Swayze et al. |
| 2016/0066914 A1 | 3/2016 | Baber et al. |
| 2016/0074040 A1 | 3/2016 | Widenhouse et al. |
| 2016/0089141 A1 | 3/2016 | Harris et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0192929 A1 | 7/2016 | Schmid et al. |
| 2016/0199063 A1 | 7/2016 | Mandakolathur Vasudevan et al. |
| 2016/0199064 A1 | 7/2016 | Shelton, IV et al. |
| 2016/0206315 A1 | 7/2016 | Olson |
| 2016/0220250 A1 | 8/2016 | Hiles et al. |
| 2016/0220257 A1 | 8/2016 | Casasanta et al. |
| 2016/0242775 A1 | 8/2016 | Shelton, IV et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0278764 A1 | 9/2016 | Shelton, IV et al. |
| 2016/0278765 A1 | 9/2016 | Shelton, IV et al. |
| 2016/0278774 A1 | 9/2016 | Shelton, IV et al. |
| 2016/0278777 A1 | 9/2016 | Shelton, IV et al. |
| 2016/0278778 A1 | 9/2016 | Shelton, IV et al. |
| 2016/0310143 A1 | 10/2016 | Bettuchi |
| 2017/0056016 A1 | 3/2017 | Barton |
| 2017/0086836 A1 | 3/2017 | Harris |
| 2017/0119388 A1 | 5/2017 | Kostrzewski |
| 2017/0231633 A1 | 8/2017 | Marczyk et al. |
| 2017/0303952 A1 | 10/2017 | Nativ |
| 2017/0354415 A1 | 12/2017 | Casasanta, Jr. et al. |
| 2018/0042611 A1 | 2/2018 | Swayze |
| 2018/0103952 A1* | 4/2018 | Aronhalt ......... A61B 17/07207 |
| 2018/0125491 A1 | 5/2018 | Aranyi |
| 2018/0229054 A1 | 8/2018 | Racenet et al. |
| 2018/0235626 A1* | 8/2018 | Shelton, IV ..... A61B 17/07292 |
| 2018/0256164 A1* | 9/2018 | Aranyi ................ A61B 17/072 |
| 2019/0247050 A1* | 8/2019 | Goldsmith ....... A61B 17/00491 |
| 2019/0290267 A1* | 9/2019 | Baxter, III ......... A61B 17/0643 |

FOREIGN PATENT DOCUMENTS

| | | |
|---|---|---|
| EP | 0327022 A2 | 8/1989 |
| EP | 0594148 A1 | 4/1994 |
| JP | 2000166933 A | 6/2000 |
| JP | 2002202213 A | 7/2002 |
| JP | 2007124166 A | 5/2007 |
| WO | 9005489 A1 | 5/1990 |
| WO | 95/16221 A1 | 6/1995 |
| WO | 98/38923 A1 | 9/1998 |
| WO | 9926826 A2 | 6/1999 |

(56) References Cited

FOREIGN PATENT DOCUMENTS

| WO | 0010456 A1 | 3/2000 |
|---|---|---|
| WO | 0016684 A1 | 3/2000 |
| WO | 2008109125 A1 | 9/2008 |
| WO | 2010075298 A2 | 7/2010 |
| WO | 2017074842 A2 | 5/2017 |

OTHER PUBLICATIONS

Extended European Search Report corresponding to counterpart Int'l Appln. No. EP 16 15 3647.9 dated Jun. 3, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln No. AU 2012250278 dated Jul. 10, 2016.
Australian Patent Examination Report No. 1 corresponding to counterpart Int'l Appln No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013l; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).

(56) References Cited

OTHER PUBLICATIONS

Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. ON 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Canadian Office Action corresponding to counterpart Int'l Appln. No. CA 2,665,206 dated Nov. 19, 2013.
Chinese Notification of Reexamination corresponding to counterpart Int'l Appln. No. CN 201010517292.8 dated Jun. 2, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16150232.3, dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report issued in European Application No. 18160809.2 dated Sep. 18, 2018.

\* cited by examiner

STRUCTURE FOR ATTACHING BUTTRESS MATERIAL TO ANVIL AND CARTRIDGE OF SURGICAL STAPLING INSTRUMENT

CROSS-REFERENCE TO RELATED APPLICATIONS

The present application is a Continuation Application claiming the benefit of and priority to U.S. patent application Ser. No. 15/454,043, filed on Mar. 9, 2017, now U.S. Pat. No. 10,368,868, the entire content of which is incorporated herein by reference.

BACKGROUND

Technical Field

The present disclosure relates to attachment systems for staple line buttress materials, and more particularly, to systems and methods for detachably securing staple line buttress materials to an anvil and a staple cartridge of a surgical stapling instrument.

Background of Related Art

Surgical stapling instruments are employed by surgeons to sequentially or simultaneously apply one or more rows of fasteners, e.g., staples or two-part fasteners, to body tissue for the purpose of joining segments of body tissue together. When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible reinforcing material or "buttress" material, between the staple and the underlying tissue. In this method, a layer of buttress material is placed against the tissue and the tissue is stapled in the conventional manner.

Accordingly, new systems and methods that are reliable and that enable easy and efficient attachment and removal of a buttress material to the surgical stapling instruments would be desirable.

SUMMARY

The present disclosure describes attachment structures for securing a buttress material to a surgical stapler that demonstrate a practical approach to meeting the performance requirements and overcoming the usability challenges associated with buttress material attachment and removal. In general, the present disclosure describes a surgical stapler that includes a handle assembly, an elongate member extending from the handle assembly, and an end effector operatively coupled with the handle assembly.

In accordance with an embodiment of the present disclosure, there is provided an end effector of a surgical stapler. The end effector includes first and second jaw members and a buttress material. The first jaw member is moveable relative to the second jaw member. The first jaw member includes a contact surface, a first projection, and a catch. The catch includes first and second fingers distal of the first projection. The second finger is biased toward the contact surface. The buttress material defines a longitudinal axis. The buttress material is releasably secured to the first jaw member. The buttress material defines first, second, and third slots formed therein. The first projection of the first jaw member is received in the first slot of the buttress material. The first finger of the catch is received in the second slot of the buttress material.

In an embodiment, the first and second fingers of the catch may be formed of an elastic material. In addition, the first and second fingers of the catch may define an acute angle with respect to each other. The second finger of the catch may include a head portion and a neck portion. The head portion may be configured to engage the contact surface of the first jaw member. The head portion may define a first width. The neck portion may define a second width smaller than the first width.

In another embodiment, the first jaw member may include an anvil assembly.

In another embodiment, the buttress material may be transitionable between an unexpanded state and an expanded state.

In another embodiment, the second and third slots of the buttress material may be adjacent to each other.

In yet another embodiment, the second slot of the buttress material may be defined transverse to the longitudinal axis of the buttress material. In addition, the third slot of the buttress material may extend along a length of the longitudinal axis of the buttress material. In addition, a proximal portion of the buttress material may be tapered.

In accordance with another embodiment of the present disclosure, there is provided an end effector of a surgical stapler including first and second jaw members and a buttress material. The first jaw member is moveable relative to the second jaw member. The first jaw member includes a contact surface and a catch having first and second fingers. The second finger biased toward the contact surface. The second jaw member includes first and second projections. The second projection is distal of the first projection. The buttress material defines a longitudinal axis. The buttress material is releasably secured with at least one of the first or second jaw members. The buttress material defines first, second, and third slots formed therein. The first projection of the second jaw member is received in the first slot of the buttress material when the buttress material is secured with the second jaw member. The first finger of the catch is received in the second slot of the buttress material when the buttress material is secured with the first jaw member, and the second projection of the second jaw member is received in the third slot of the buttress material when the buttress material is secured with the second jaw member.

In accordance with yet another embodiment of the present disclosure, there is provided a buttress material for use with a surgical stapling instrument. The buttress material includes an elongate body defining a longitudinal axis. The elongate body includes proximal and distal portions. The proximal portion includes a tapered portion. Further, the proximal portion defines first and second proximal slots separated by a wall. The first and second proximal slots extend transverse to the longitudinal axis. In addition, the distal portion defines first and second distal slots. In particular, the first distal slot is defined transverse to the longitudinal axis, and the second distal slot extends along a length of the longitudinal axis. The second distal slot is distal of the first distal slot.

BRIEF DESCRIPTION OF THE DRAWINGS

The accompanying drawings illustrate embodiments of the disclosure and, together with a general description of the disclosure given above, and the detailed description of the embodiment(s) given below, serve to explain the principles of the disclosure, wherein.

DETAILED DESCRIPTION

Figure 1:
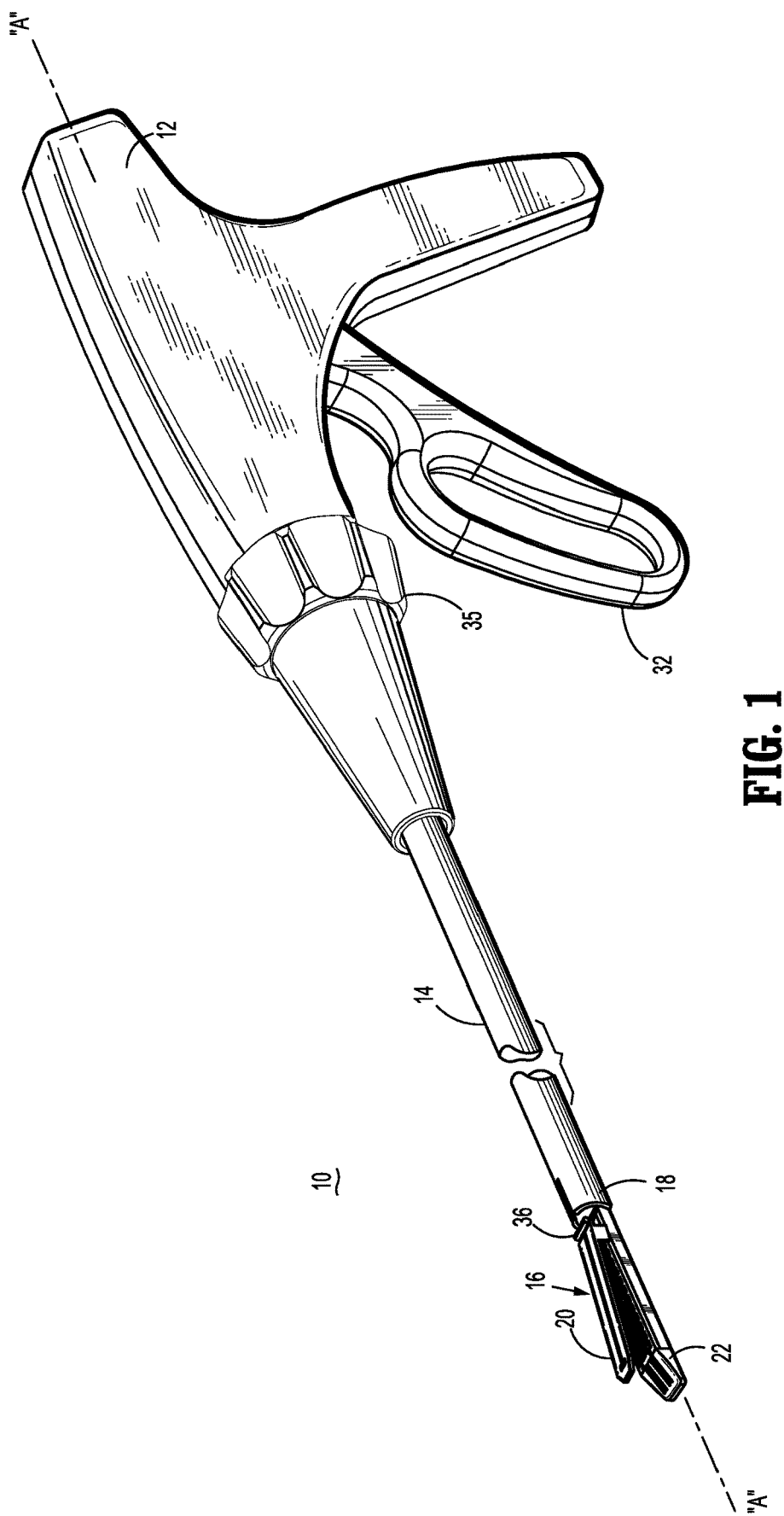
FIG. 1 is a perspective view of a surgical stapling instrument including buttress retention assemblies for attaching buttress materials to an anvil and a staple cartridge of the surgical stapling instrument in accordance with an embodiment of the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

With reference to FIG. 1, there is provided a surgical stapler 10 for use in stapling tissue and applying a layer of buttress material between staples and underlying tissue. Surgical stapler 10 generally includes a handle 12 and an elongate tubular member 14 extending distally from handle 12. A jaw assembly 16 is mounted on a distal end 18 of elongate tubular member 14. Jaw assembly 16 includes an anvil 20 and a staple cartridge 22. Anvil 20 is movable between an open position configured to receive tissue "T" (FIG. 8) between anvil 20 and staple cartridge 22 and a closed position configured to clamp "T" between anvil 20 and staple cartridge 22.

With continued reference to FIG. 1, surgical stapler 10 includes a trigger 32 movably mounted on handle 12. Actuation of trigger 32 is configured to move anvil 20 from the open position to the closed position and subsequently actuate surgical stapler 10 to apply lines of staples 178 (FIG. 9) to tissue "T". In order to provide proper orientation of jaw assembly 16 relative to tissue to be stapled, surgical stapler 10 is additionally provided with a rotation knob 35 mounted on handle 12. Rotation of rotation knob 35 about a longitudinal axis "A-A" of surgical stapler 10 rotates elongate tubular member 14 and jaw assembly 16 about longitudinal axis "A-A."

Figure 2:
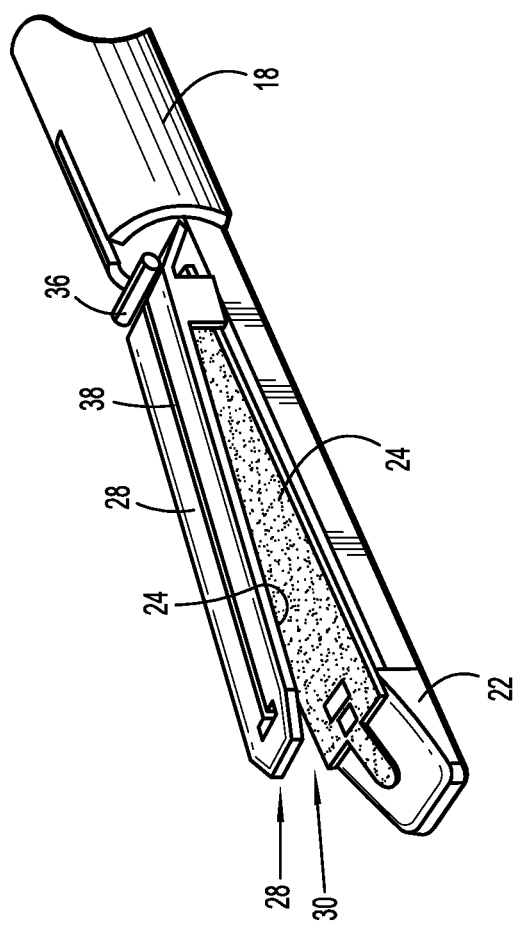
FIG. 2 is a perspective view of a jaw assembly of the surgical stapling instrument of FIG. 1, illustrating a buttress material secured with the staple cartridge.

With reference now to FIG. 2, a driver 36 is provided to move anvil 20 between the open and closed positions relative to staple cartridge 22. Driver 36 moves along a longitudinal slot 38 defined in anvil 20. A knife blade 70 (FIGS. 4 and 5) is associated with driver 36 to cut tissue "T" captured between anvil 20 and staple cartridge 22 as driver 36 passes through longitudinal slot 38. In order to secure staples 178 (FIG. 9) provided by staple cartridge 22 about tissue "T" and buttress materials 24, anvil 20 is provided with longitudinally arranged rows of staple clinching or forming pockets 44 (FIG. 9) located on either side of longitudinal slot 38. Reference may be made to U.S. Pat. No. 7,128,253, filed on Jul. 20, 2005, entitled "Surgical Stapler," the entire content of which is incorporated herein by reference, for a detailed discussion of the construction and operation of surgical stapler 10.

Figure 3:
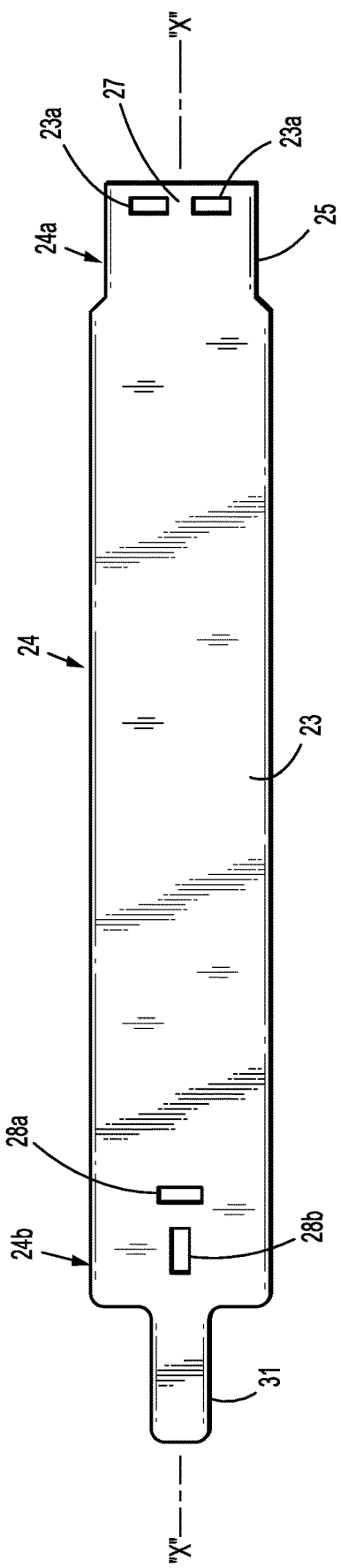
FIG. 3 is a top view of the buttress material of FIG. 2 configured for use with the anvil and the staple cartridge of the surgical stapling instrument of FIG. 1.

With reference to FIG. 3, there is provided a buttress material 24 in accordance with the present disclosure. Buttress material 24 reinforces and seals staple lines applied to tissue "T" by surgical stapler 10. Buttress material 24 is configured for use with both anvil 20 and staple cartridge 22. Buttress material 24 may be detachably secured with anvil 20 or staple cartridge 22. Buttress material 24 includes an elongate body 23 having proximal and distal portions 24a, 24b. In particular, proximal portion 24a includes a tapered portion 25 defining proximal slots 23a separated by a wall 27. Each proximal slot 23a is defined transverse to a longitudinal axis "X-X" defined by buttress material 24. Distal portion 24b of buttress material 24 defines a first distal slot 28a and a second distal slot 28b distal of the first distal slot 28a. First distal slot 28a is defined transverse to longitudinal axis "X-X" defined by buttress material 24, and second distal slot 28b is extends along a length of longitudinal axis "X-X". First and second distal slots 28a, 28b may be, e.g., orthogonal, to each other. In addition, buttress material 24 further includes a tab 31 configured to facilitate gripping of buttress material 24 by the clinician.

Figure 4:
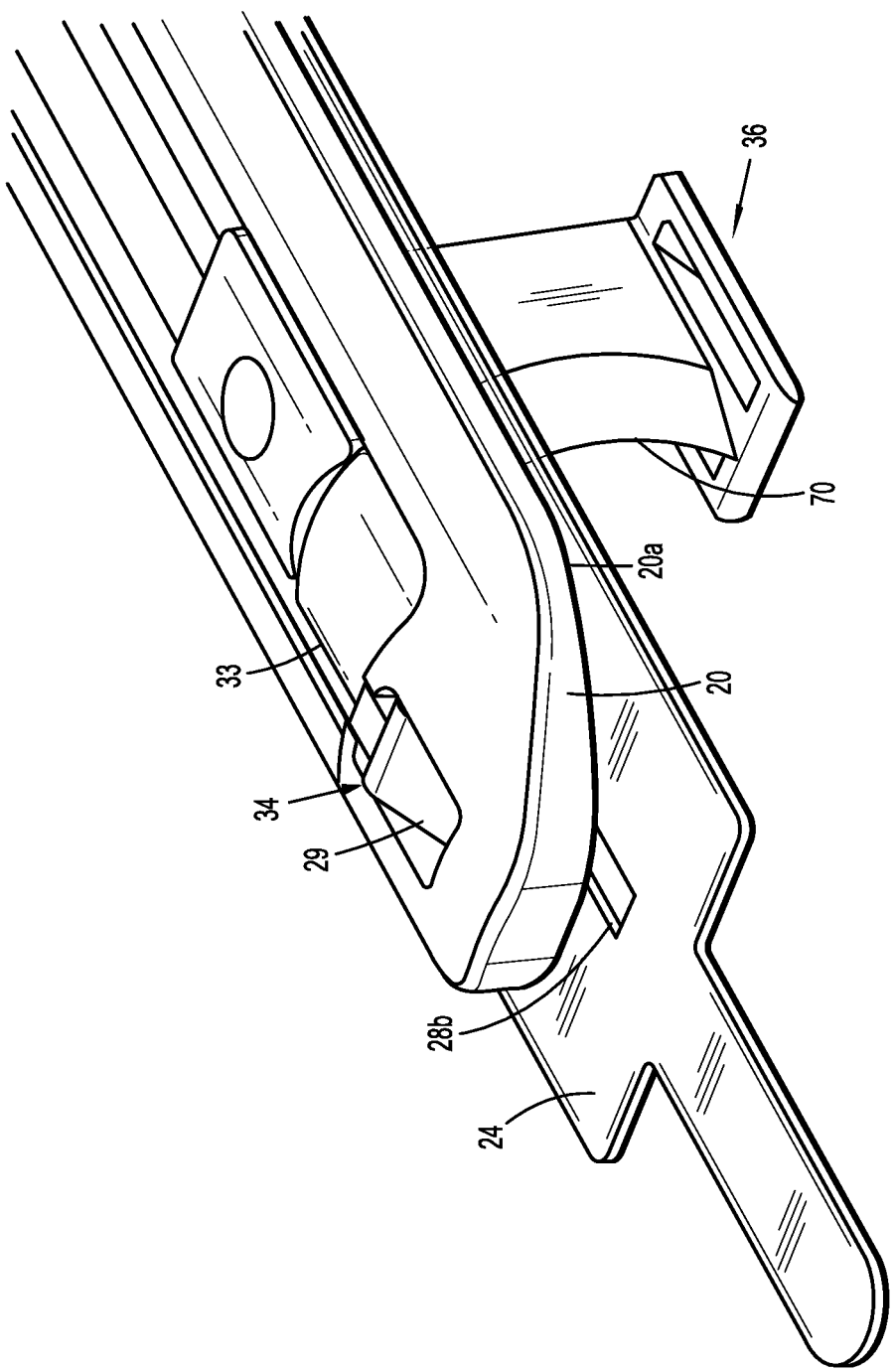
FIG. 4 is a partial perspective view of the anvil and the buttress material of FIG. 3 in accordance with an embodiment of the present disclosure.
Figure 5:
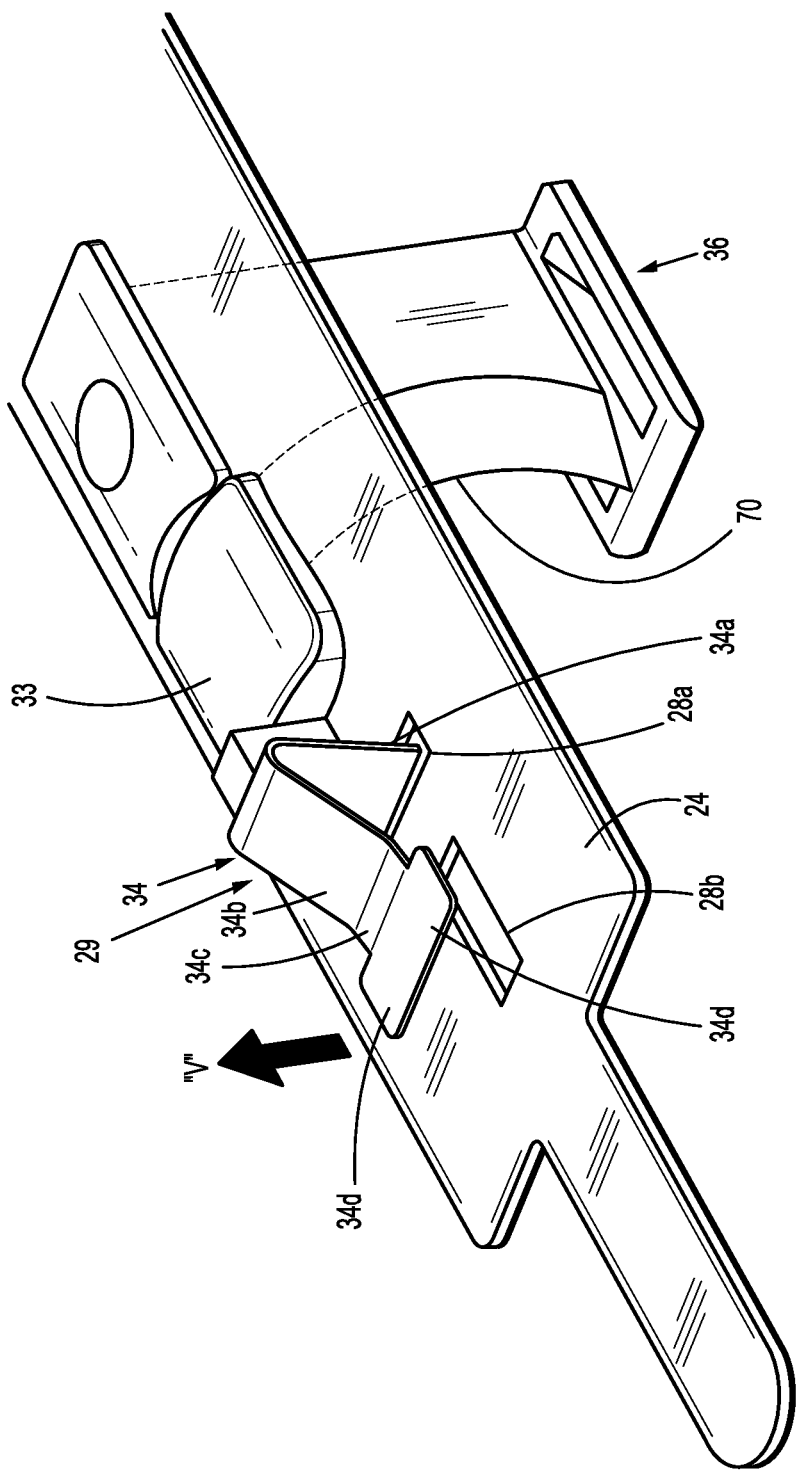
FIG. 5 is a partial perspective view of the buttress material and an anvil buttress retention assembly of FIG. 4.

With reference now to FIGS. 4 and 5, anvil 20 includes a buttress retention assembly 29. In particular, buttress retention assembly 29 includes a support or sled 33 and a resilient catch 34 extending from support 33. Catch 34 include first and second fingers 34a, 34b. A portion of first finger 34a is dimensioned to be received within first distal slot 28a of buttress material 24. First finger 34a may define an angle of about 5 degrees with respect to an axis perpendicular to longitudinal axis "X-X" of buttress material 24. First finger 34a may be configured to substantially inhibit relative movement between buttress material 24 and first finger 34a in, e.g., longitudinal and/or lateral directions. First and second fingers 34a, 34b may define an acute angle with respect to each other. Catch 34 further includes a neck portion 34c extending from second finger 34b and a head portion 34d extending from neck portion 34c. Head portion 34d of catch 34 is configured to engage contact surface 20a (FIG. 4) of anvil 20 to stabilize first finger 34a received within first distal slot 28a of buttress material 24.

In particular, first and second fingers 34a, 34b of catch 34 are formed of elastic and/or compressible material to enable flexing to facilitate engagement and/or disengagement of first and second fingers 34a, 34b with/from respective first distal slot 28a of buttress material 24 and contact surface 20a of anvil 20. Furthermore, second finger 34c of catch 34 may be biased toward contact surface 20a of anvil 20 in the direction of arrow "V" (FIG. 5) to further enhance securement of buttress material 24 on anvil 20.

In addition, a proximal portion of anvil 20 may further include proximal protrusions 20b (FIG. 9) such as, e.g., bosses or hooks, extending proximally outward from contact surface 20a of anvil 20. Proximal protrusions 20b are dimensioned to be received in respective proximal slots 23a of buttress material 24. Proximal slots 23a and first distal slot 28a of buttress material 24 are positioned such that in order to place the proximal protrusions 20b of anvil 20 into respective proximal slots 23a and to place first finger 34a of catch 34 into first distal slot 28a of buttress material 24, buttress material 24 is stretched to the expanded state and proximal protrusions 20b are forced through respective proximal slots 23a and first finger 34a is received through first distal slot 28a. In this manner, once buttress material 24 is secured with anvil 20, buttress material 24 may be released from the expanded state to transition towards the unexpanded state which, in turn, provides securement of buttress material 24 on anvil 20. Such a configuration maintains buttress material 24 taut across contact surface 20a of anvil 20 and facilitates passage of surgical stapler 10 into the body of a patient as surgical stapler 10 is inserted into and manipulated within the body of the patient.

Figure 6:
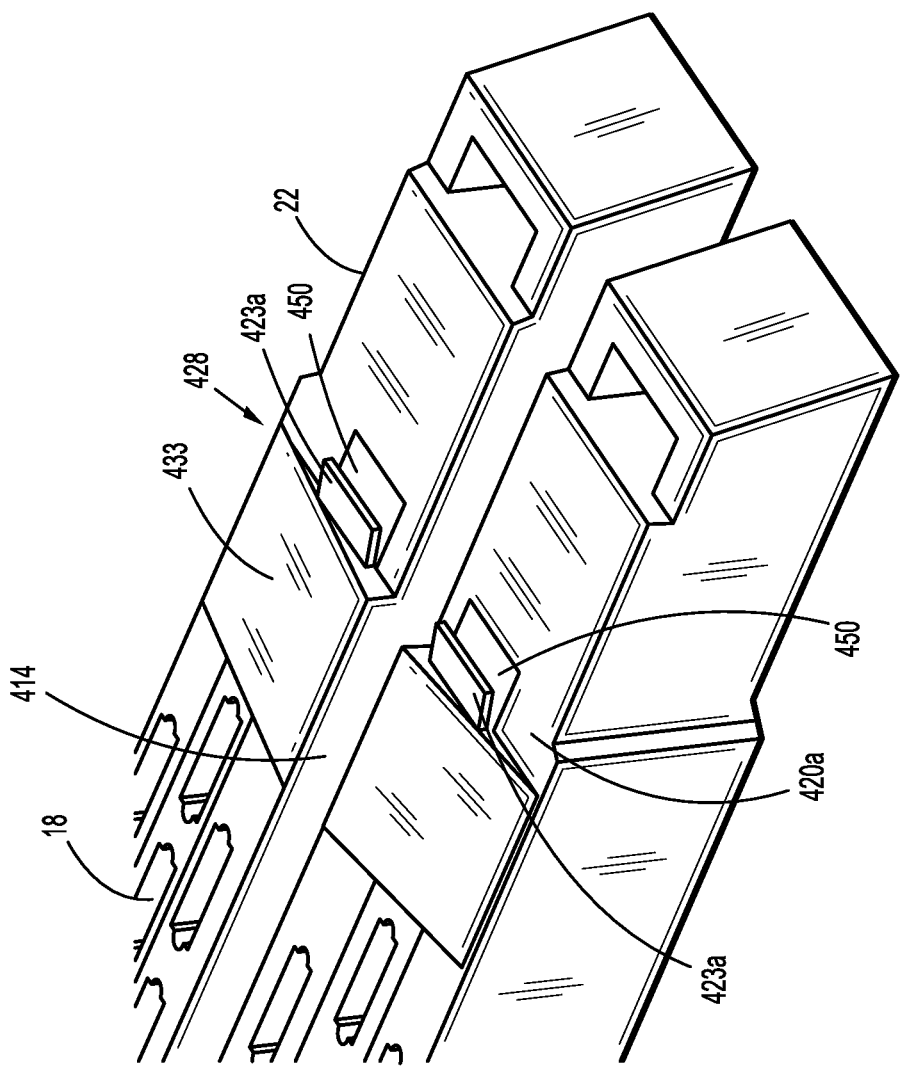
FIG. 6 is a partial perspective view of a proximal portion of the staple cartridge of the surgical stapling instrument of FIG. 1.
Figure 7:
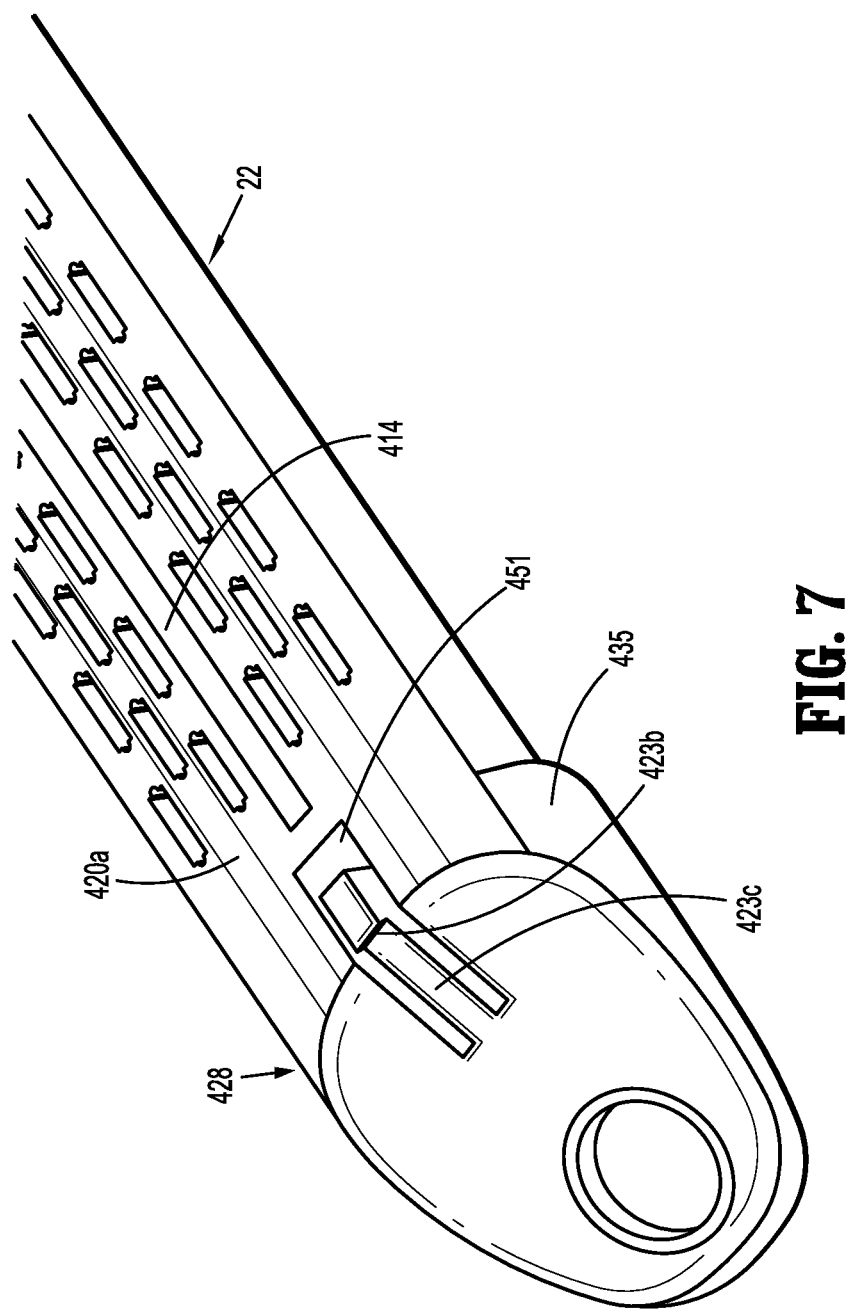
FIG. 7 is a partial perspective view of a distal portion of the staple cartridge of the surgical stapling instrument of FIG. 1.

With reference to FIGS. 6 and 7, buttress material 24 may also be mounted on staple cartridge 22 prior to stapling of tissue "T". Buttress material 24 reinforces and seals staple lines applied to tissue "T" by surgical stapler 10. Staple cartridge 22 is provided with rows of staple pockets 18 and a knife channel 414 that passes longitudinally between rows of staple pockets 18. Staple cartridge 22 includes a cartridge buttress retention assembly 428 including proximal fingers 423a disposed on opposing sides of knife channel 414. Staple cartridge 22 includes a mount 433 that is transversely sloped or angled. Proximal fingers 423a extend proximally from mount 433. Mount 433 may be configured to provide a planar contact with buttress material 24 thereon. A gap 450 is defined between each proximal finger 423a and a contact surface 420a of staple cartridge 22 to receive buttress material 24 therein. In particular, proximal fingers 423a are configured to be received through respective proximal slots 23a (FIG. 3) of buttress material 24.

With particular reference now to FIG. 7, a distal end portion 435 of staple cartridge 22 defines a cavity 451 dimensioned to receive a finger 423c. Cartridge buttress retention assembly 428 includes a distal tooth 423b extending from finger 423c. Finger 423c is configured for slight flexing to facilitate engagement and disengagement of buttress material 24 on tooth 423b. In addition, distal tooth 423b is dimensioned to be received through second distal slot 28b (FIG. 3) of buttress material 24.

In use, with reference back to FIGS. 3 and 5, the proximal protrusions 20b (FIG. 9) in the proximal portion of anvil 20 are inserted through proximal slots 23a of buttress material 24. Thereafter, elastic buttress material 24 is stretched to the expanded state such that first finger 34a of catch 34 is received through first distal slot 28a to thereby secure buttress material 24 with anvil 20. Alternatively, buttress material 24 may also be secured with staple cartridge 22 as discussed hereinabove.

Figure 8:
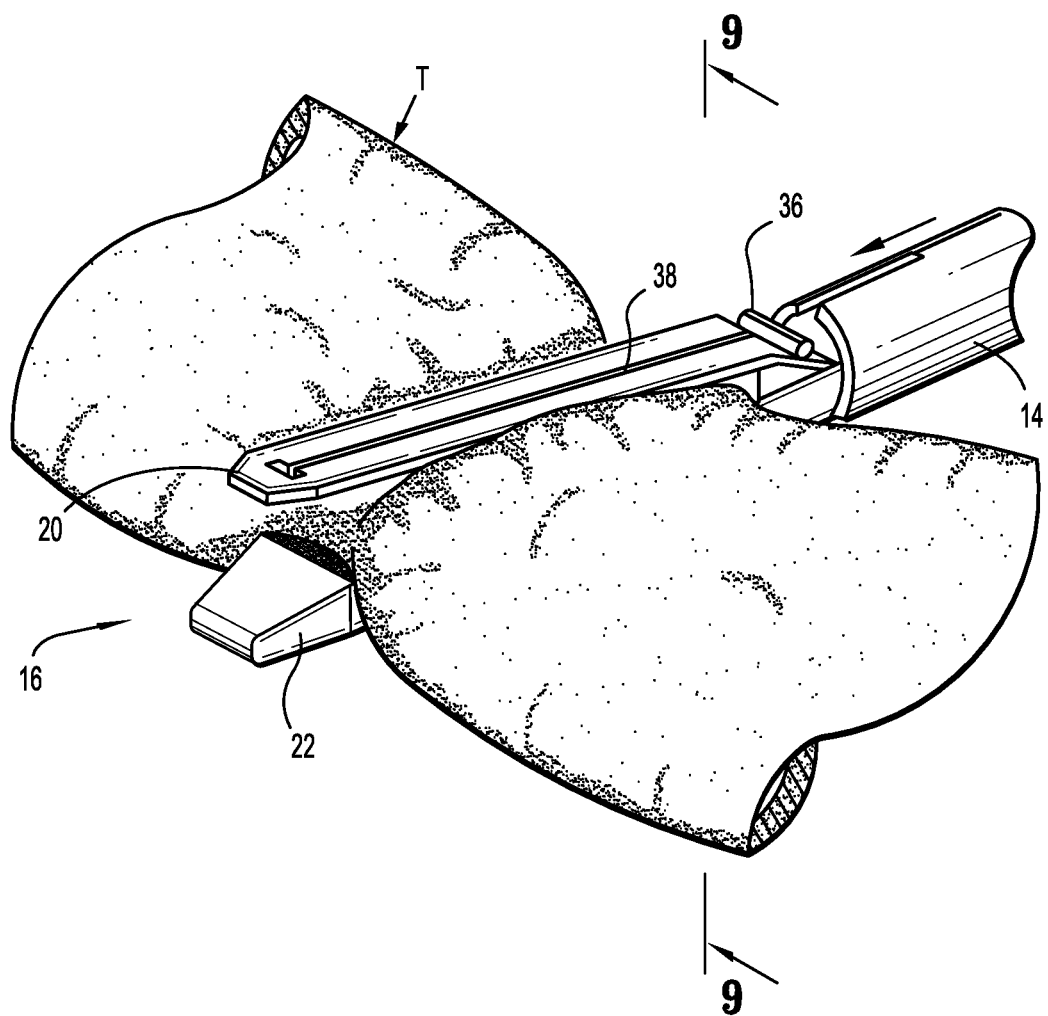
FIG. 8 is a perspective view of a distal end of the surgical stapling instrument of FIG. 1.
Figure 9:
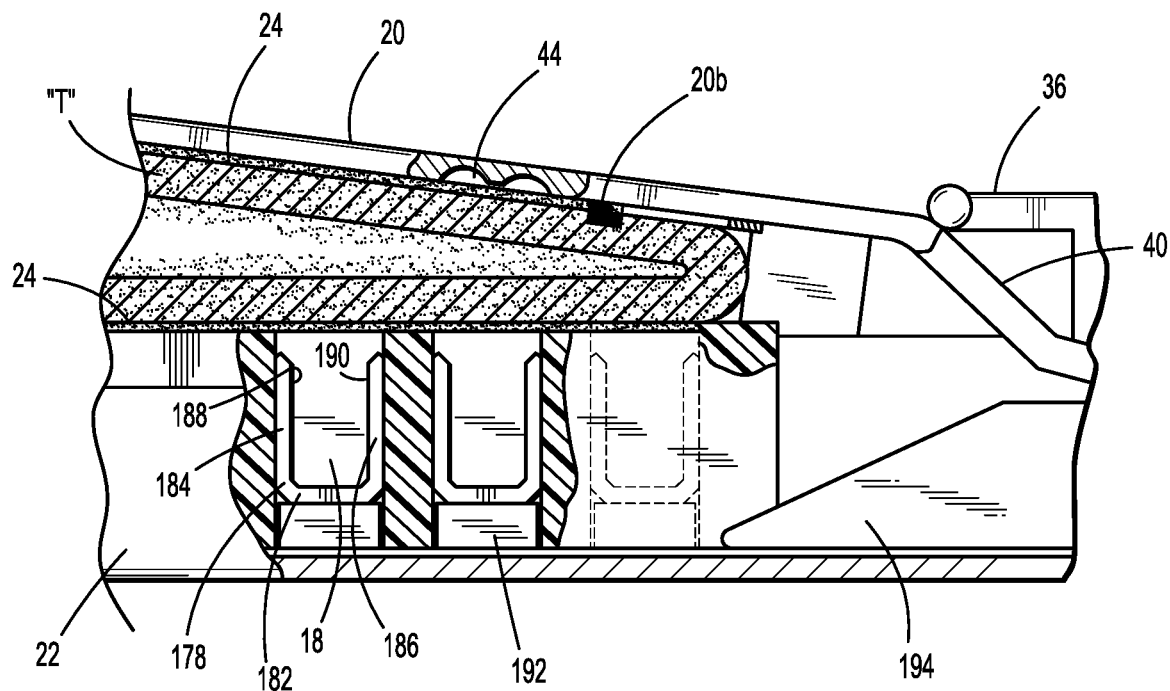
FIG. 9 is a partial cross-sectional view of the distal end of the surgical stapling instrument as taken through 9-9 of FIG. 8.
Figure 10:
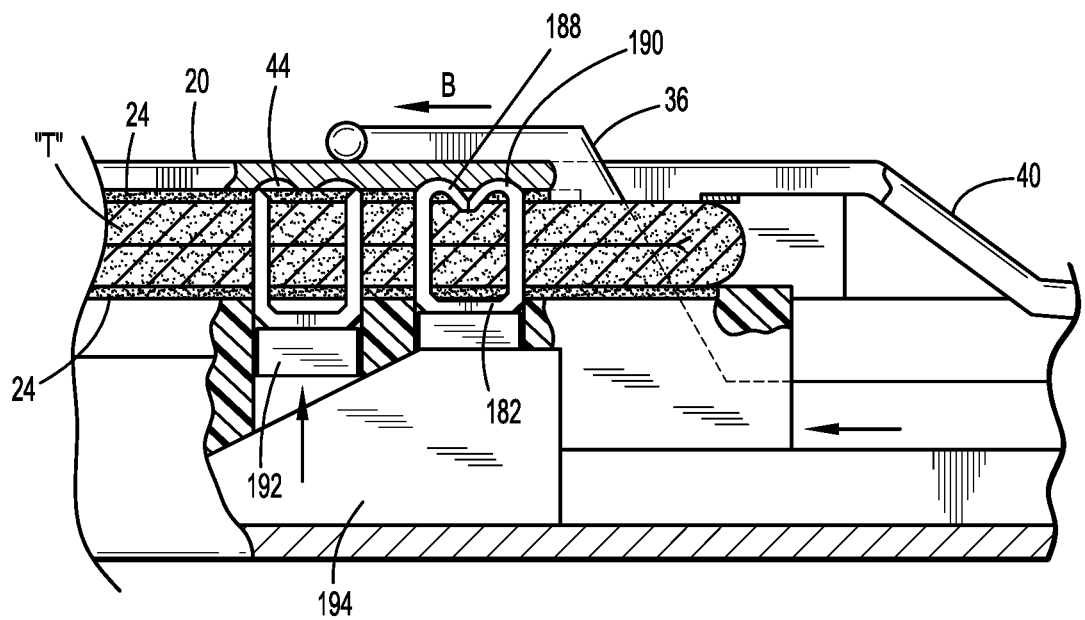
FIG. 10 is a partial cross-sectional view of the distal end of the surgical stapling instrument of FIG. 9, illustrating actuation of the surgical stapling instrument.
Figure 11:
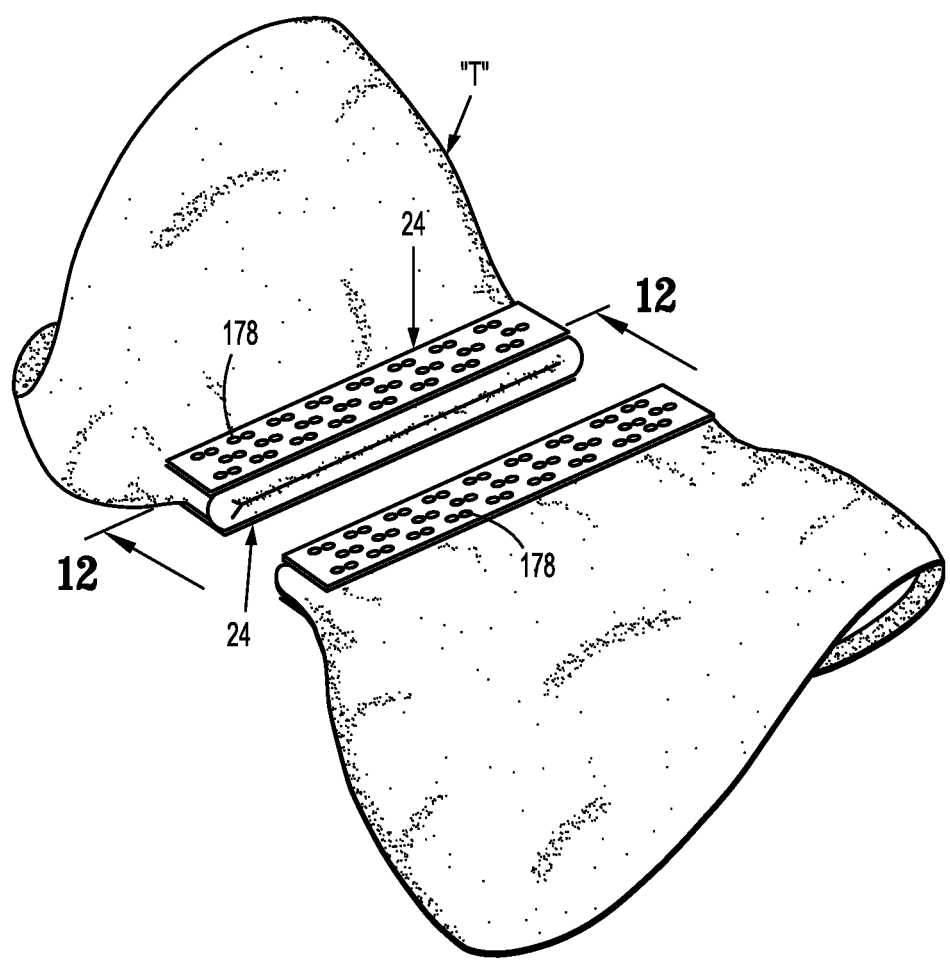
FIG. 11 is a perspective view of a stapled and divided tissue section.
Figure 12:
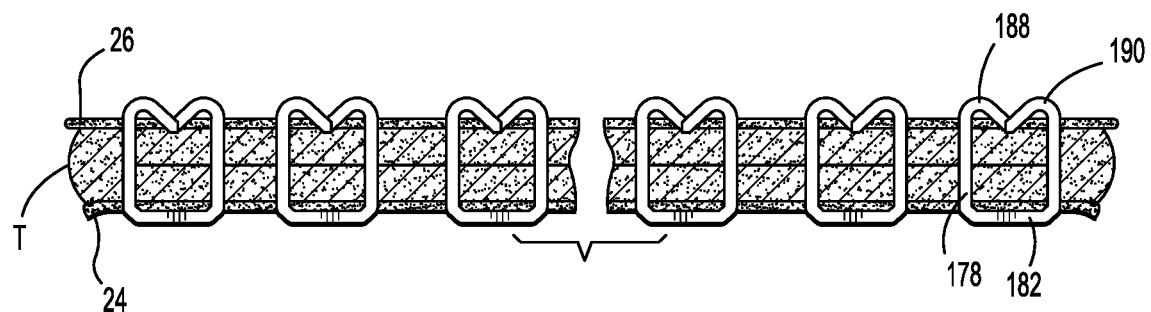
FIG. 12 is a cross-sectional view of the stapled and divided tissue section as taken through 12-12 of FIG. 11.

With reference now to FIGS. 8-10, jaw assembly 16 is positioned adjacent tissue "T" to be stapled. Driver 36 is in a proximal position relative to anvil slot 38. Staple cartridge 22 includes staples 178 positioned within respective staple pockets 18. Staples 178 are of a conventional type and include a backspan 182 having a pair of legs 184 and 186 extending from backspan 182. Legs 184 and 186 terminate in tissue penetrating tips 188 and 190. Pushers 192 are located within staple pockets 18 and are positioned between staples 178 and the path of a drive bar 194.

With particular reference to FIGS. 9 and 10, surgical stapler 10 is initially actuated by movement of trigger 32 relative to handle 12 (FIG. 1) causing driver 36 to move in the direction of arrow "B" and against sloped edge 40 of anvil 20 thereby causing anvil 20 to be moved to the closed position relative to staple cartridge 22. As drive bar 194 advances distally, drive bar 194 urges pushers 192 upwardly against backspans 182 of staples 178 driving staples 178 through buttress material 24 mounted on staple cartridge 22, tissue "T", and buttress material 24 mounted on anvil 20 and towards staple clinching pockets 44 in anvil 20. Tissue penetrating tips 188 and 190 are bent within staple clinching pockets 44 in anvil 20 to thereby secure buttress material 24 mounted on anvil 20 against tissue "T" while backspan 182 secures buttress material 24 mounted on staple cartridge 22 against tissue "T".

Upon full actuation of surgical stapler 10, knife blade 70 (FIG. 5) associated with surgical stapler 10 and carried by driver 36 cuts tissue "T", as well as buttress materials 24 on opposing sides of tissue "T", between the rows of now clinched staples 178. In addition, driver 36 operatively engages support 33 of buttress retention assembly 29 and causes concomitant movement of support 33. The distal movement of support 33 causes first finger 34a of catch 34 to be disengaged from first distal slot 28a of buttress material 24 to facilitate release of buttress material 24 from anvil 20.

Upon movement of anvil 20 to the open position spaced apart from staple cartridge 22, buttress materials 24 pull away from respective anvil 20 and staple cartridge 22. The resulting tissue "T" is divided and stapled with staples 178. Specifically, buttress material 24 that was mounted on staple cartridge 22 is secured against tissue "T" by backspans 182 of staples 178 and buttress material 24 that was mounted on anvil 20 is secured against tissue "T" by the now clinched tissue penetrating tips 188 and 190 of staples 178. In this manner, buttress materials 24 are stapled to tissue "T" thereby sealing and reinforcing the staple lines created by staples 178.

Buttress material 24 may have a substantially elongate rectangular profile. It is further contemplated that buttress material 24 may have a relatively thin, planar profile. In addition, buttress material 24 may be made from any biocompatible natural or synthetic material. The material from which the buttress material is formed may be bioabsorbable or non-bioabsorbable. It should of course be understood that any combination of natural, synthetic, bioabsorbable and non-bioabsorbable materials may be used to form the buttress material.

Some non-limiting examples of materials from which the buttress material may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the buttress material. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material.

The buttress material may be porous or non-porous, or combinations of porous and non-porous layers. Where the buttress material is non-porous, buttress material may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like.

In embodiments, the buttress material is porous and possesses hemostatic properties. Where the buttress material is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where the buttress material is porous, the pores may be formed using any method suitable to forming a foam or sponge including, but not limited to the lyophilization or freeze-drying of a composition. Suitable techniques for making foams are within the purview of those skilled in the art. Porous buttress materials can be at least 0.2 cm thick, in embodiments from about 0.3 to about 1.5 cm thick. Porous buttress materials can have a density of not more than about 75 mg/cm$^2$ and, in embodiments below about 20 mg/cm$^2$. The size of the pores in the porous buttress materials can be from about 20 μm to about 300 μm, in embodiments from about 100 μm to about 200 μm.

The buttress material may also include a reinforcement member. The reinforcement member may be associated with a porous or non-porous layer or may be positioned between a non-porous layer and a porous layer of the buttress material. Alternatively, the reinforcement member may be positioned entirely within one or more of the individual layers (i.e., embedded within the porous layer, the non-porous layer, or both) of the buttress material. It is also envisioned that the reinforcement member may be positioned at the surface of one of the layers making up the buttress material and, in embodiments, may be positioned at an exterior surface of the buttress material.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the buttress material has randomly oriented chopped fibers that have not been previously fused together embedded within in the buttress material.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect such as a compound that affects or participates in tissue growth, cell growth, or cell differentiation.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the buttress material in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-viral s; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Persons skilled in the art will understand that the structures and methods specifically described herein and shown in the accompanying figures are non-limiting exemplary embodiments, and that the description, disclosure, and figures should be construed merely as exemplary of particular embodiments. For example, the projections of anvil or staple cartridge may be slightly larger in size than the apertures or slots of buttress materials, thereby providing an interference fit upon insertion of the projections into the apertures or slots. The projections and the corresponding apertures and slots may have any geometry best suited for retaining the projections within the apertures or slots. In addition, various numbers of fingers or projections may be provided to increase the frictional contact between a jaw member and an associated buttress material.

It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An end effector of a surgical stapler comprising:
   first and second jaw members, the first jaw member including a contact surface, a first projection, and a catch including first and second fingers distal of the first projection, the second finger biased toward the contact surface; and
   a buttress material releasably securable to the first jaw member, the buttress material defining a first distal slot, wherein the first finger of the catch is configured to be received in the first slot of the buttress material.

2. The end effector according to claim 1, wherein the buttress material includes an elongate body defining a longitudinal axis and including proximal and distal portions, the proximal portion being tapered along the longitudinal axis.

3. The end effector according to claim 2, wherein the proximal portion of the elongate body of the buttress material defines first and second proximal slots separated by a wall.

4. The end effector according to claim 3, wherein the first projection of the first jaw member is configured to be received in the first or second proximal slots of the buttress material.

5. The end effector according to claim 3, wherein the first and second proximal slots of the buttress material extend transverse to the longitudinal axis defined by the buttress material.

6. The end effector according to claim 1, wherein the first distal slot of the buttress material is defined transverse to a longitudinal axis defined by the buttress material.

7. The end effector according to claim 1, wherein the buttress material further defines a second distal slot extending along a length of the longitudinal axis, the second distal slot distal of the first distal slot.

8. The end effector according to claim 7, wherein the buttress material includes a tab distal of the second distal slot.

9. The end effector according to claim 1, wherein the buttress material is configured to expand along a longitudinal axis defined by the buttress material.

10. The end effector according to claim 1, wherein the buttress material is formed of a resilient material.

11. The end effector according to claim 1, wherein at least a portion of the catch is formed of an elastic material.

12. An end effector of a surgical stapler comprising:
    a first jaw member including a contact surface and a catch biased towards the contact surface;
    a second jaw member including first and second projections, at least one of the first or second jaw members movable relative to the other one of the first or second jaw members; and a buttress material formed of a resilient material, the buttress material defining first, second, and third slots, the first and second slots configured to receive respective first and second projections of the second jaw member when the buttress material is longitudinally stretched, the third slot configured to receive the catch when the buttress material is releasably secured with the first jaw member.

13. The end effector according to claim 12, wherein the catch of the first jaw member includes first and second fingers formed of an elastic material.

14. The end effector according to claim 13, wherein the first and second fingers of the catch define an acute angle with respect to each other.

15. The end effector according to claim 13, wherein the second finger of the catch includes a head portion and a neck portion, the head portion defining a first width, the neck portion defining a second width smaller than the first width.

16. The end effector according to claim 12, wherein the first jaw member includes an anvil assembly.

17. The end effector according to claim 12, wherein the third slot of the buttress material is defined transverse to a longitudinal axis defined by the buttress material.

18. The end effector according to claim 12, wherein the first slot of the buttress material is defined along a longitudinal axis defined by the buttress material.

19. The end effector according to claim 12, wherein a proximal portion of the second jaw member includes a transversely sloped mount.

\* \* \* \* \*